(12) United States Patent
Cowe (10) Patent No.: US 9,119,920 B2
(45) Date of Patent: Sep. 1, 2015

(54) AUTOMATIC INJECTION DEVICE WITH PNEUMATIC DAMPING

(75) Inventor: Toby Cowe, Oxford (GB)

(73) Assignee: OWEN MUMFORD LIMITED, Oxford (GB)

(*) Notice: Subject to any disclaimer, the term of this patent is extended or adjusted under 35 U.S.C. 154(b) by 20 days.

(21) Appl. No.: 13/979,705

(22) PCT Filed: Jan. 6, 2012

(86) PCT No.: PCT/GB2012/050016
§ 371 (c)(1),
(2), (4) Date: Aug. 8, 2013

(87) PCT Pub. No.: WO2012/098371
PCT Pub. Date: Jul. 26, 2012

(65) Prior Publication Data
US 2013/0317447 A1    Nov. 28, 2013

(30) Foreign Application Priority Data
Jan. 17, 2011    (GB) .................... 1100678.0

(51) Int. Cl.
*A61M 5/20*    (2006.01)
*A61M 5/32*    (2006.01)
(Continued)

(52) U.S. Cl.
CPC ............ *A61M 5/3202* (2013.01); *A61M 5/2033* (2013.01); *A61M 2005/202* (2013.01);
(Continued)

(58) Field of Classification Search
CPC .......... A61M 5/20; A61M 2005/3247; A61M 2005/1581; A61M 2005/206; A61M 2005/3261; A61M 2005/3264; A61M 2005/3267; A61M 2005/2013; A61M 2005/325; A61M 2005/3254; A61M 2005/1426; A61M 2005/3249; A61M 2205/581; A61M 25/0618; A61M 25/0631; A61M 5/2033
USPC ......... 604/110–111, 117, 134–137, 156–157, 604/187, 192, 196–198, 225
See application file for complete search history.

(56) References Cited

U.S. PATENT DOCUMENTS 5,092,842 A * 3/1992 Bechtold et al. ............... 604/135
6,270,479 B1 * 8/2001 Bergens et al. ............... 604/156
(Continued)

FOREIGN PATENT DOCUMENTS

CH    468 196 A    2/1969
EP    1 586 341 A2    10/2005
(Continued)

OTHER PUBLICATIONS
International Search Report, dated Apr. 2, 2012, from corresponding PCT application.
(Continued)

*Primary Examiner* — Bhisma Mehta
*Assistant Examiner* — Brandy S Lee
(74) *Attorney, Agent, or Firm* — Young & Thompson (57) ABSTRACT

An injection device for use with a syringe having a syringe body, a needle coupled thereto, and a plunger moveable through the body to eject medication from the syringe through the needle, includes a housing defining an inner space for holding a syringe and facilitating movement thereof from a first position in which the needle is contained fully within the housing and a second position in which the needle projects from the housing, and a drive member located within the inner space so that in use the drive member can engage the plunger of a syringe held within the housing. The device further includes a force applicator located within the inner space for providing a force to the drive member so as to move the syringe from the first to the second position and thereafter to move the plunger through the syringe body, a trigger mechanism, and a damper.

12 Claims, 6 Drawing Sheets

(51) Int. Cl.
    *A61M 5/24*    (2006.01)
    *A61M 5/31*    (2006.01)

(52) U.S. Cl.
    CPC .... *A61M2005/206* (2013.01); *A61M 2005/208* (2013.01); *A61M 2005/2086* (2013.01); *A61M 2005/2418* (2013.01); *A61M 2005/3142* (2013.01)

(56) References Cited

U.S. PATENT DOCUMENTS

| | | |
|---|---|---|
| 6,454,743 B1 | 9/2002 | Weber |
| 2001/0044847 A1 | 11/2001 | Kirchhofer et al. |
| 2003/0105430 A1 | 6/2003 | Lavi et al. |
| 2013/0046233 A1 | 2/2013 | Green |

FOREIGN PATENT DOCUMENTS

| | | |
|---|---|---|
| GB | 2 414 398 A | 11/2005 |
| WO | 94/21316 A1 | 9/1994 |
| WO | 99/33504 A1 | 7/1999 |
| WO | 00/24441 A1 | 5/2000 |
| WO | 03/035149 A1 | 5/2003 |
| WO | 03/097133 A1 | 11/2003 |
| WO | 2004/000395 A1 | 12/2003 |
| WO | 2005/025636 A2 | 3/2005 |
| WO | 2009/047247 A1 | 4/2009 |
| WO | 2009/141219 A1 | 11/2009 |
| WO | 2010/146358 A2 | 12/2010 |

OTHER PUBLICATIONS

GB Search Report, dated Mar. 30, 2011, from corresponding GB application.

* cited by examiner

AUTOMATIC INJECTION DEVICE WITH PNEUMATIC DAMPING

TECHNICAL FIELD

The present invention relates to injection devices of the type used to inject medication into patients. In particular, the invention relates to the provision of a damping mechanism within such injection devices.

BACKGROUND

Spring driven injection devices are known and used to assist patients and medical professionals with the injection of medications held in conventional plunger driven syringes. Such injection devices typically comprise a housing for containing the syringe to which a needle is fixed, and a drive member attached to a relatively strong compression spring for driving the plunger into the syringe body to eject medication through the needle and into a patient.

Figure 1:
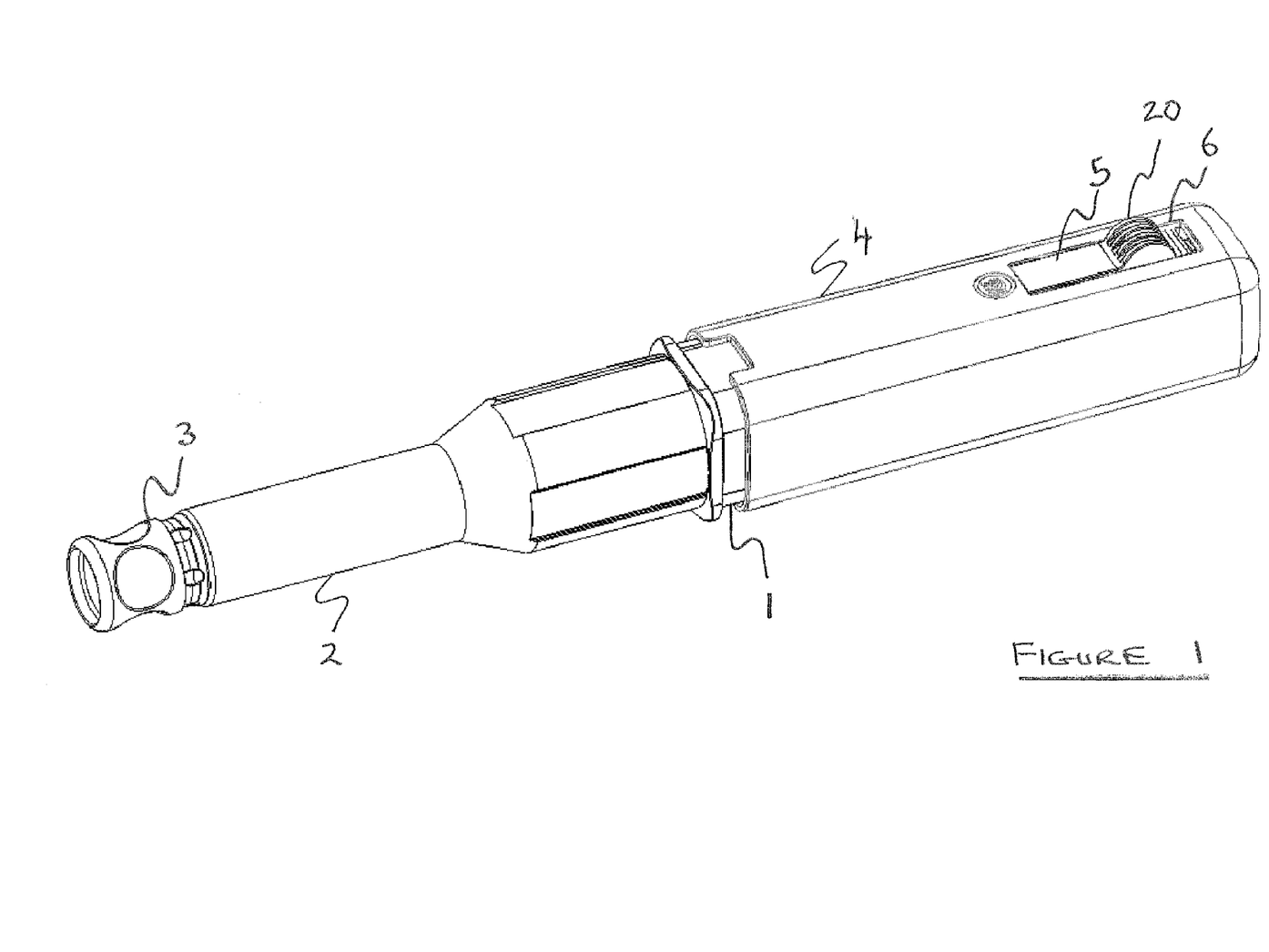
FIG. 1 illustrates schematically a prior art injection device for use with a standard syringe.

By way of example, International patent application publication number WO94/21316 describes an injection device substantially as illustrated in FIG. 1. This device is intended to completely eject all medication from a syringe, i.e. it has no mechanism for adjusting the ejected dose. The injection device comprises a distal housing part 1 into which is screwed a proximal housing part 2 (where the terms "distal" and "proximal" are used here and in the following text to identify respectively locations distant from and close to a patient's skin when the device is in use). An adjustable needle shield 3 is further screwed into a proximal end of the proximal housing part 2. A housing sleeve 4 is slideably mounted on top of the distal housing part 1. As is shown in FIG. 1, the injection device comprises a trigger 5 which projects through a window 6 provided in the sleeve 4.

Figure 2:
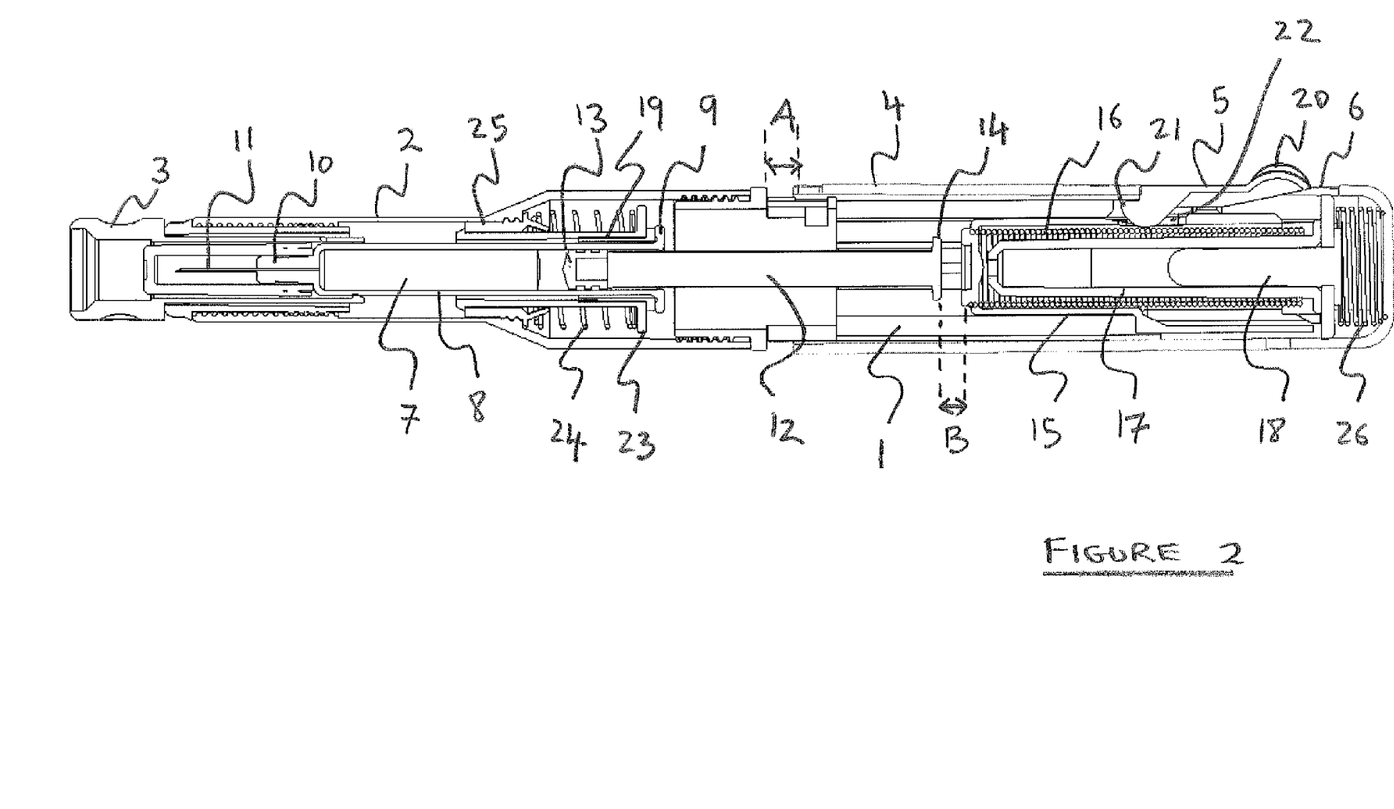
FIG. 2 shows a cross-section through the prior art injection device of FIG. 1.

FIG. 2 illustrates the prior art device of FIG. 1 in cross-section. The device is shown with a syringe 7 located within the housing, where the syringe comprises a syringe body 8 having a pair of radially extending "wings" 9 at one end and a needle coupling 10 formed at the other end. A needle 11 is shown attached to the syringe body using the needle coupling 10. The syringe also comprises a plunger 12 having a rubber bung 13 attached to one end and an enlarged end face or plate 14 formed at the other end to assist in pushing the plunger through the syringe body. The syringe is supported within the proximal housing part 2 by a short support tube 19 that sits coaxially within the proximal housing part 2. A collar 23 is provided around the distal end of the support tube 19, and provides an end stop for a relatively light coil spring 24. The other end of the coil spring 24 is stopped by a locking tube 25 which is screwed to an interior surface of the proximal housing part 1. The locking tube 25 also fixes the support tube 19 into the proximal housing part 2 such that this support tube is fixed relative to the proximal housing part.

As shown in FIG. 2, a drive member 15 is slideably located within the distal housing part 1. The drive member is generally cylindrical having a generally square cross-section. Located within the interior space of the drive member 15 is a relatively strong compression drive spring 16. The drive spring is supported on a cylindrical support shaft 17 which is in turn fixably attached to the distal housing part 1 via an elongate pin 18.

FIG. 2 illustrates the device in the primed or cocked position, where the drive member 15 has been pushed into the distal housing part 1 in the distal direction, thereby compressing the drive spring 16 along the support shaft 17. FIG. 2 shows the trigger 5 pivotally coupled to the distal housing part 1 and partially projecting through the window 6 formed in the sleeve 4. The trigger comprises at an outer distal end thereof a button part 20 and, at an inner proximal part, a catch 21. In the position illustrated in FIG. 2, the catch 21 is engaged with a corresponding recess 22 formed in the drive member 15 such that the drive member is held by the trigger in the primed state. Although not shown in the figures, the trigger 5 is biased about its pivot axis such that the catch is pressed against the drive member 15 in the absence of any external force.

In order to release the drive member 15 from the primed state and thereby push the needle 11 into a patient's skin and inject medication from the syringe 7, a user holds the sleeve 4 in a fist-like grip and presses the needle shield 3 against his or her skin. This causes the sleeve 4 to slide over the distal housing part housing 1, closing the gap identified in FIG. 2 with the reference A. This relative movement of the sleeve and the distal housing part causes the window 6 to move wholly over the trigger 5 such that, when the user exerts pressure on the trigger button part 20 with his or her thumb, the trigger pivots, disengaging the catch 21 from the recess 22. Once the drive member 15 is released, the force exerted by the expanding drive spring 16 pushes the drive member 15 forward and into engagement with the end plate 14 of the syringe plunger 12.

At this stage in the operation of the device, the syringe body 8 is relatively free to move through the proximal housing part 2 such that the force exerted by the drive member 15 on the plunger end plate 14 causes the entire syringe 7 to move towards the distal end of the injection device. The wings 9 formed on the end of the syringe body 8 act on the support tube collar 23, causing the support tube 19 to also move towards the proximal end of the device, compressing the relatively light coil spring 24. Once this spring is fully compressed, further movement of the support tube 19 and therefore of the syringe body 8 is prevented. Of course, during this preliminary phase, the needle is projected beyond the end of the needle shield and into the patient's skin. The extent to which the needle projects beyond the end of the needle shield 3 can be adjusted by screwing the shield into and out of the proximal end of the proximal housing part 2.

As the driver member 15 continues to exert a significant force on the plunger 12 after further movement of the support tube 19 and the syringe body 8 has been prevented, the plunger 12 begins to move through the syringe body 8 thereby ejecting medication through the needle 11.

It is noted that the device illustrated in FIGS. 1 and 2 comprises a further, relatively light compression spring 26 that is connected between the distal housing part 1 and the sleeve 4. This spring 26 is relatively light, and allows the sleeve 4 to be returned to its original position once an injection has been completed and the user has both removed the needle shield 3 from contact with the skin and has released the pressure on the trigger button 20.

In order to assemble the device of FIGS. 1 and 2, the proximal and distal housing parts are separated, and a complete syringe including medication is dropped into the proximal housing part through the larger open end thereof so that it is supported within the support tube 19. With the housing parts still separated, the drive member 15 is pressed into the distal housing part 1 (using, for example, a cocking tool) until the catch 21 on the trigger 5 engages with the drive member recess 22 and locks the drive member in the cocked position. The device can then be assembled by screwing the proximal and distal housing parts together.

In order to take into account different tolerances within the injection device and the syringe, the injection device is configured such that, when the device is fully assembled, a small gap is present between the end plate 14 of the plunger 12 and the opposed end of the drive member 15. This gap is identified in FIG. 2 with the reference B. In the absence of such a gap, the drive member could come into contact with the end plate of the plunger during connection of the housing parts, causing some movement of the syringe through the lower housing towards the distal end of the device. It is also possible that some initial sticking of the syringe body could occur, resulting in the ejection of a small volume of medication from the syringe.

A potential problem observed in the prior art device such as that illustrated in FIGS. 1 and 2 arises from the relatively high force exerted by the drive member 15 on the syringe plunger 12. A high force is of course required in order to eject the medication through the needle and into the patient. However, the initial impact caused by the drive member 15 hitting the end plate 14 of the syringe plunger 12 may damage the plunger and or the drive member. For example, it is possible that the end of the plunger may fracture. It is also possible that the collar 23 formed on the support tube 19 and/or the syringe wings 9 may be damaged when the spring 24 is compressed to its full extent, i.e. immediately prior to injection of medication from the syringe.

SUMMARY

It is an object of the present invention to overcome or at least mitigate the problems identified with known injection devices including the problem discussed above. This object is achieved by incorporating a damping mechanism into the device such that the kinetic energy imparted by the drive member to the syringe plunger is reduced during an initial operating phase.

According to a first aspect of the present invention there is provided an injection device for use with a syringe having a syringe body, a needle coupled to the syringe body, and a plunger which can be moved through the syringe body to eject medication from the syringe through the needle. The injection device comprises a housing defining an inner space for holding a syringe and facilitating movement of the syringe from a first position in which the needle is contained fully within the housing and a second position in which the needle projects from the housing, and a drive member located within said inner space so that in use the drive member can engage the plunger of a syringe held within the housing. The device further comprises a force applicator located within said inner space for providing a force to the drive member so as to move the syringe from said first to said second position and thereafter to move the plunger through the syringe body, a trigger mechanism for retaining the spring and the drive member in a cocked configuration and, upon activation, for releasing the spring and the drive member, and a damper for damping the kinetic energy imparted by the drive member to the syringe plunger during all or a part of the movement of the syringe from said first to said second position.

Due to the damping of the drive member, impact forces on the syringe are reduced, thereby reducing the risk of damage to the syringe and the device during use.

The housing may comprise a first housing part for holding said syringe and facilitating said movement of the syringe, and a second housing part having a second coupling for engagement with said first coupling to secure the first and second housing parts together, said drive member being located within the second housing part so that in use the drive member can engage the plunger of a syringe held within the first housing part. Alternatively, the housing may comprise a single main body part. The housing may further comprise a needle shield adjustably coupled to other housing parts.

The force applicator may be one of:
a compression spring;
a torsion spring; and
an electrically driven applicator.

The damper may be configured to damp kinetic energy imparted by the drive member to the syringe plunger from a cocked position of the plunger, substantially until the syringe has reached said second position. The damper may be one of:
a pneumatic damper;
a hydrodynamic damper; and
and a friction damper.

The damper may be a pneumatic damper comprising a piston having a piston head in engagement with said drive member and a cylinder within which the piston is mounted, said piston and cylinder defining a chamber and one of the piston and cylinder defining a passage for delimiting a first fluid flow path into and out of said chamber. Said piston and cylinder may be configured such that movement of the piston outwardly with respect to the cylinder beyond a point defined by said second position creates a second fluid flow path into said chamber, reducing or eliminating damping of the drive member. The piston and cylinder may be further configured so that the inner surface of an end of the cylinder tapers radially outward with respect to an end of said piston, thereby establishing said second fluid flow path into said chamber following outward movement of the piston within the cylinder beyond a predefined point.

The device may comprise an O-ring mounted on an external surface of said piston or on an internal surface of said cylinder and forming a substantially airtight seal between the piston and the cylinder up to said predefined point.

Where said force applicator comprises a spring, said cylinder may be provided by a spindle fixedly coupled to said second housing part, with said spring being coaxially mounted around the outside of the spindle. The piston may extend coaxially inside said spring.

The piston head being fixed to the drive member. Alternatively, the piston may be formed integrally with said drive member.

The force applicator may comprises a spring, with said drive member being generally cylindrical and defining an inner space within which said spring is located. The trigger mechanism may be configured to engage with said drive member.

DETAILED DESCRIPTION

There will now be described, with reference to FIGS. 3 to 6 of the accompanying drawings, an improved injection device that is suitable for use with a standard syringe 7 such as has already been described with reference to FIGS. 1 and 2. Such a syringe includes a generally cylindrical syringe body 8 having provided at a proximal end thereof a coupling for attachment of a needle. The syringe body is provided at its distal end with pair of radially extending wings 9, intended to aid holding of the syringe during manual use. The syringe 7 has a needle 11 attached to the needle coupling, whilst a plunger 12 is inserted into the distal end of the syringe body 8 and projects therefrom. As is well known in the art, the plunger 12 has a bung 13 attached to the end that is inserted into the syringe body 8 in order to seal a medication contained with the syringe body 8.

The improved injection device is able to re-use certain components of known devices. In particular, in the embodiment that will now be described, the proximal device part including the proximal housing part 1, needle shield 3, support tube 19, locking tube 25, and coil spring 24, is substantially identical to that described with reference to FIGS. 1 and 2. Modifications to the known device primarily concern distal device part. In the following discussion, it is assumed that the distal device component illustrated in FIGS. 3 to 6 is merely connected to the proximal device part of the injection device of FIGS. 1 and 2 using the respective screw threads.

Figure 3:
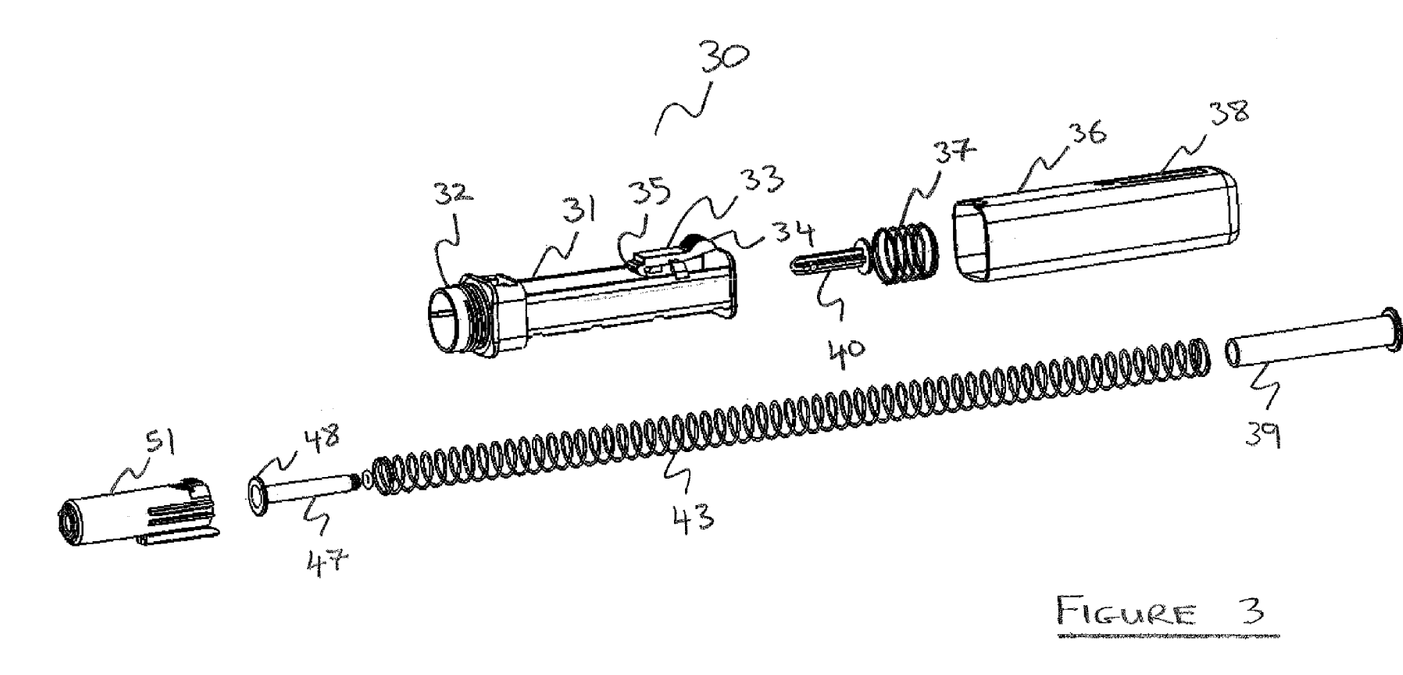
FIG. 3 shows an exploded view of a distal part of an injection device, including a drive member damping mechanism.
Figure 4:
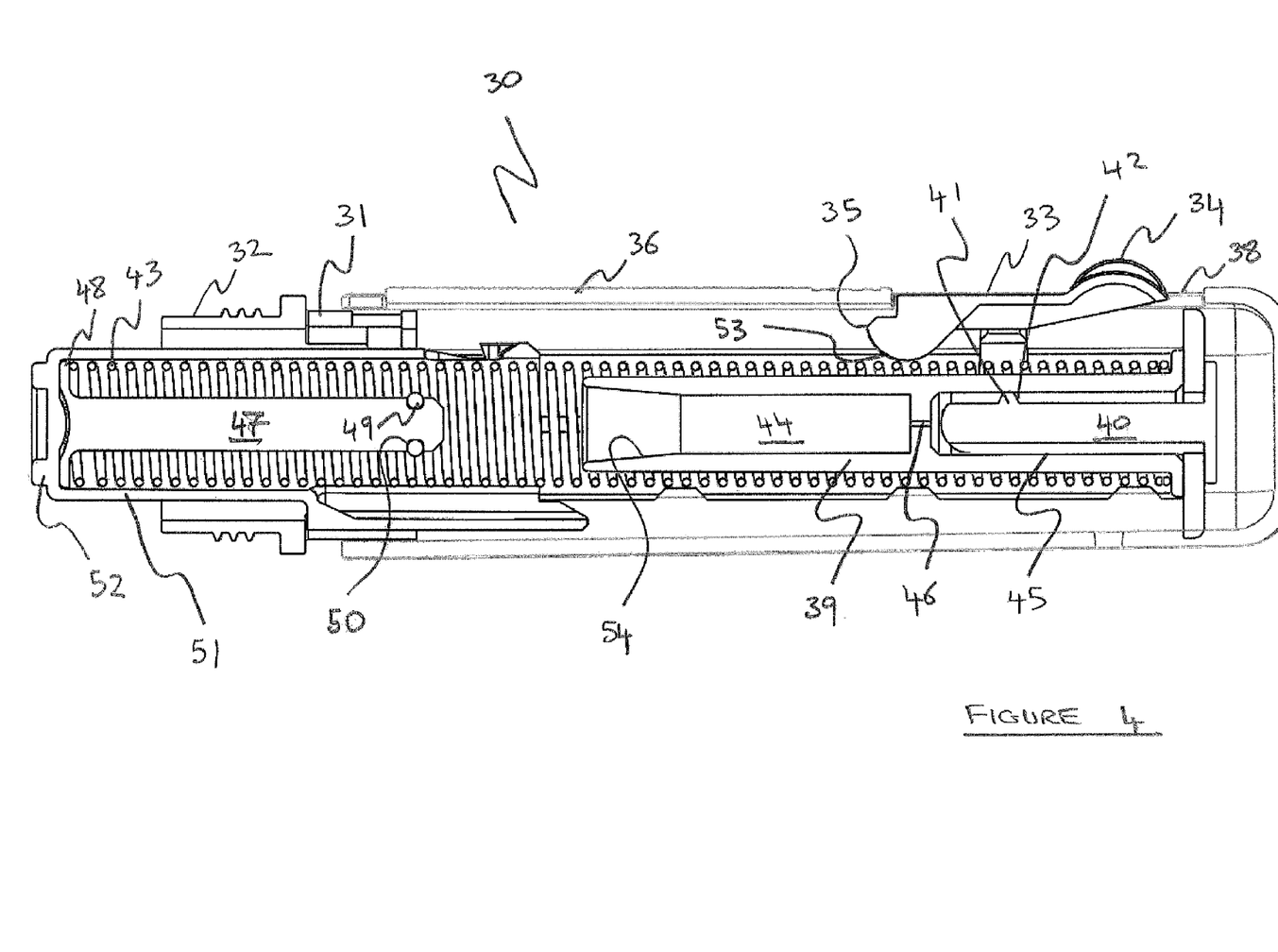
FIG. 4 shows a cross-sectional view of the distal part of FIG. 3, assembled and in an uncocked state.

Referring first to FIGS. 3 and 4, the distal device part 30 comprises a distal housing part 31 that has a generally cylindrical shape with a rectangular cross-section. At the distal end 32 of the distal housing part 31 (that is the leftmost end as illustrated in the Figure), the cross-section changes to circular to provide a coupling having a screw thread formed around its outer surface suitable for engagement with the screw thread formed on an inner surface of a proximal device part. A trigger 33 is formed integrally with the distal housing part 31 and is provided with a trigger button 34 at one end and a catch 35 at the other end. The trigger is able to pivot about a central pivot access. The trigger 33 is formed such that, when a pressure is applied to the trigger button 34 in a radially inward direction, the catch 35 moves in a radially outward direction, such that a subsequent release of this pressure results in the trigger 33 returning to its original position. The operation of the trigger 33 is thus broadly in line with that described with reference to FIGS. 1 and 2.

The distal housing part 31 is contained within a sleeve 36, with a light coil spring 37 interposed between an end face of the distal housing part 31 and an inner end face of the sleeve 36. The sleeve 36 is formed with a window 38 through which a part of the trigger 33, including the trigger button 34, projects. A generally cylindrical support shaft 39 is centrally mounted along the axis of the device, within the distal housing part 31. The support shaft 39 is held in place by an elongate locking pin 40, with a bump 41 on the locking pin 40 engaging a recess 42 formed on an inner surface of the support shaft 39 (see FIG. 4). A main drive spring 43 is located coaxially over the support shaft 39 and is free to move over the support shaft in the absence of any further restrictions. The support shaft 39 is formed such that a central, cylindrical space within the spindle is separated into a proximal chamber 44 and a distal chamber 45. The chambers 44, 45 are connected via a channel 46 having a relatively small diameter such that the chambers are in fluid communication with one another. The various components of the distal device part 30 are such that air is able to enter the distal chamber 45 from the exterior of the device.

A piston 47 having a generally cylindrical cross-section is inserted into one end of the drive spring 43. The piston 47 has an enlarged, generally circular head 48 at its proximal end, the outer diameter of the head 48 being slightly greater than the outer diameter of the drive spring 43. When the drive spring 43 is compressed, the body of the piston 47 is centrally located within the proximal chamber 44 of the support shaft such that said proximal chamber 44 provides a cylinder 44 within which the piston can move. An "O" ring 49 is located around the circumference of one end of the piston 47, and is held in place by a circumferentially extended groove 50 formed around the surface of the piston.

The O-ring 49 ensures an essentially air tight fit for the piston 47 within the proximal chamber or cylinder 44 whilst allowing the piston to move axially within the cylinder 44. Other means for sealing the piston to the cylinder 44 will be readily apparent to the skilled person.

A generally cylindrical drive member 51 having a generally circular cross-section encloses the drive spring 43 and the piston 47. The drive member 51 has a closed distal end face 52 which butts against and is fixed to the piston head 48. The drive member 51 has a recess 53 formed therein such that, when the drive member is pushed into the distal housing part 31 to thereby compress the drive spring 43, the trigger catch 35 engages the recess 53 and locks the drive member 51 in a cocked position. As already described, once engaged with the recess 53, the trigger catch 35 is held in place by locking engagement of the sleeve 36.

Figure 5:
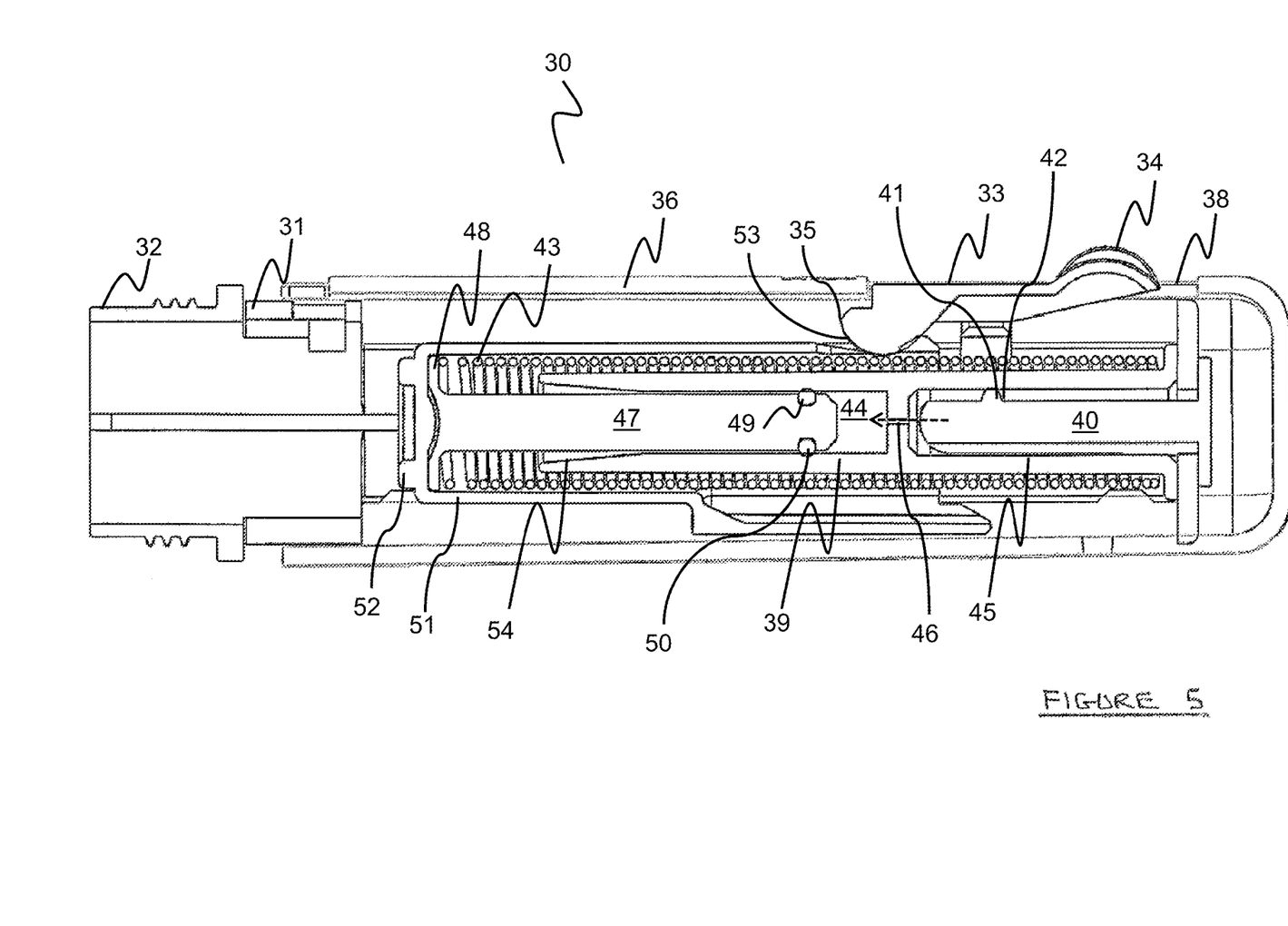
FIG. 5 shows a cross-sectional view of the assembled distal part of FIG. 4 in a cocked state.

FIG. 4 illustrates the distal device part 30 in an initial, uncocked state. In this state, the distal device part 30 would not be attached to the proximal device part (of FIGS. 1 and 2). In order to prime the distal device part, the user presses the drive member 51 into the distal housing part 31, for example using a suitable cocking tool. The drive member 51 is pushed into the distal housing part until the trigger catch 35 snaps into place, locking the components together. This cocked state of the device is illustrated in FIG. 5 from which it can be seen is that the drive spring 43 is almost in its fully compressed state. At this stage, and as discussed above, the device is assembled by first dropping a syringe 7 containing medication into the proximal device part. The proximal and distal device parts are then connected together by engaging and closing the respective screw threads.

Once the device is fully assembled, as with the device of FIGS. 1 and 2, a small gap B is present between the end face 52 of the drive member 51 and the opposed end of the syringe plunger 12 (for simplicity, the syringe is not shown in FIGS. 3 to 6). In this state, the piston 47 is largely contained within the proximal chamber 44 of the support shaft 39. Once assembled, the device is ready for use by a patient.

As has already been discussed, a patient uses the device by holding the sleeve in a fist-like grip and pressing the end of the needle shield against his or her skin. This causes the sleeve 36 to slide over the distal housing part 31 in a direction towards the patient's skin, in turn causing the window 38 to open over the trigger catch 35. The user then presses his or her thumb against the trigger button 34 causing the trigger 33 to pivot, raising the trigger catch 35 from the drive member recess 53. The drive spring 43 begins to expand axially and in the proximal direction, pushing first the piston 47 and in turn the drive member 51 axially towards the distal end of the device. In the initial drive phase, movement of the piston 47 through the proximal chamber 44 causes air to be sucked into that chamber through the small channel 46 connecting the proximal and distal chambers. As the diameter of this channel 46 is relatively small, the flow of air between the chambers is restricted, resulting in a damping of the movement of the piston 47 through the proximal chamber and therefore a damping of the movement of the drive member 51. In effect, this damps the kinetic energy applied by the piston 47 to the plunger 12. The impact of the piston head 48 on the plunger end plate 14 is therefore significantly reduced as compared to the impact from an undamped drive member (FIGS. 1 and 2).

Movement of the piston 47 continues to be damped after impact on the plunger end plate 14, i.e. during movement of the syringe 7 through the proximal device part. The result is that the syringe needle 11 is inserted into the patient's skin at a slower rate than would otherwise be the case. Movement of the piston is damped right up to the point at which the collar 23 of the support tube 19 comes into contact with the locking tube 25, such that the impact of the collar 23 on the locking tube 25, and the impact of the syringe wings 9 on the collar 23, is considerably reduced. Thus, as compared with the known devices, the risk of damage to the device as a result of these impacts is reduced.

The dimensions of the piston 47 and of the proximal chamber 44 are such that, at or about this point in the operation phase, the end of the piston within the proximal chamber enters a tapered or fluted end region 54 of the proximal chamber. A gap appears between the piston and the chamber wall such that air is able to flow around the surface of the O-ring 49 and into the proximal chamber 44. This air flow is significant as compared to the air flow through the interconnecting channel 46, such that movement of the piston 47 within the proximal chamber 44 is no longer damped to any significant extent (other than by the resistance presented by the plunger 12). The full expansion force of the drive spring 43 is therefore exerted on the drive member 51 such that the drive member 51 accelerates movement of the plunger 12 into the syringe body 8. The increased force is sufficient to inject medication through the needle 11 at the desired rate.

Figure 6:
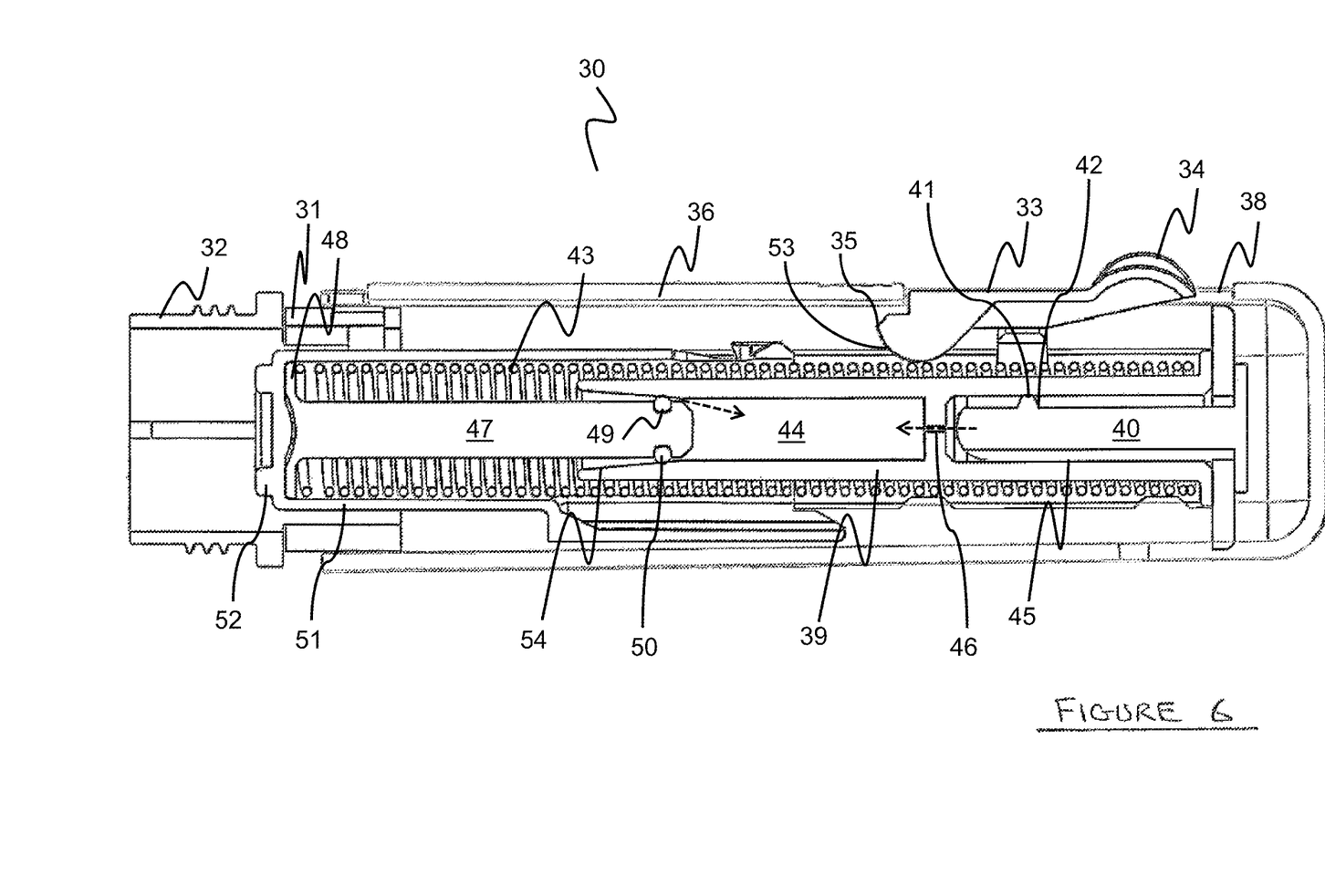
FIG. 6 shows a cross-sectional view of the assembled distal part of FIG. 4 in an intermediate firing state.

FIG. 6 illustrates the configuration of the distal device part 30 at the point where the needle begins to project from the needle shield (not shown in the Figure) and at the point where movement of the syringe body through the proximal device part is stopped. As described, at this point the O-ring 49 affixed to the piston 47 has just entered the fluted end region 54 of the proximal chamber. Advancement of the drive member 51 into the proximal housing part continues up to and beyond the point at which the entire piston 47 lies outside of the proximal chamber 44 of the support shaft 39. Eventually, and as described above, the drive member 51 reaches the end of its stroke and delivery of medication from the syringe is completed. At this point, the distal device part 30 is in the configuration shown in FIG. 4. The user can now remove the needle from his or her skin, disconnect the proximal and distal device parts, and remove the used syringe and needle. If required, a new syringe can be dropped into the proximal device part, the distal device part cocked, and the device reassembled ready for use.

It will be appreciated by the person skilled in the art that various modifications may be made to the above described embodiment without departing from the scope of the present invention. In particular, the skilled person will appreciate that other approaches to dampen the movement of the drive member during an initial operational phase may be used. For example, rather than damping the movement of the piston by restricting the flow of air into the proximal chamber or piston cylinder, damping may be achieved by providing appropriate fictional engagement between an outer surface of the piston and an inner surface of the chamber, with that frictional restriction being removed at or about the point where the plunger begins to move through the syringe. Other modifications include: including a one-way valve into the channel 46 such that air can flow easily out of the proximal chamber 44 through the channel, but not in the reverse direction—this causes the piston and cylinder to operate like an air spring; using a fluid other than air in the damping mechanism; using a force applicator other than a compression spring to push the drive member, e.g. a torsion spring or electrically operated applicator; and forming the housing as a single part device (including an adjustable needle shield).

The invention claimed is:

1. An injection device for use with a syringe that has a syringe body provided with radially extending wings at a distal end thereof, a needle coupled to a proximal end of the syringe body, and a plunger movable through the syringe body to eject medication from the syringe through the needle, the injection device comprising:
   a housing defining an inner space sufficient for holding the syringe and facilitating movement of the syringe from a first position in which the needle is contained fully within the housing and a second position in which the needle projects from the housing;
   a support tube (19) located within the housing and within which the syringe is supported, a distal end of the support tube comprising a collar (23);
   a coil spring (24) supported between said collar and the housing such that the wings of the syringe body act on the collar to compress the compression spring (24), said second position being defined by full compression of the coil spring;
   a drive member located within said inner space so that in use the drive member can engage the plunger of the syringe within the housing;
   a force applicator located within said inner space for providing a force to the drive member which in turn acts on the plunger so as to move the syringe from said first position to said second position and thereafter to move the plunger through the syringe body;
   a trigger mechanism for retaining the force applicator and the drive member in a cocked configuration and, upon activation of said trigger mechanism, for releasing the force applicator and the drive member; and
   a pneumatic damper for damping kinetic energy imparted by the drive member to the syringe plunger during all or a part of the movement of the syringe from said first position to said second position,
   said pneumatic damper comprising a piston having a piston head in engagement with said drive member and a cylinder within which the piston is mounted, said piston and cylinder defining a chamber and one of the piston and cylinder defining a passage for delimiting a first fluid flow path into and out of said chamber, the piston and cylinder being further configured such that movement of the piston outwardly with respect to the cylinder beyond a point defined by said second position creates a second fluid flow path into said chamber, which at least reduces damping of the drive member, during ejection of medication from the syringe through the needle.

2. The injection device according to claim 1, wherein said housing comprises a first housing part for holding said syringe and facilitating said movement of the syringe, and a second housing part having a second coupling for engagement with said first coupling to secure the first and second housing parts together, said drive member being located within the second housing part so that in use the drive member can engage the plunger of a syringe held within the first housing part.

3. The injection device according to claim 1, said housing further comprising a needle shield adjustably coupled to other housing parts.

4. The injection device according to claim 1, wherein said force applicator is one selected from the group consisting of:

a compression spring,
a torsion spring, and
an electrically driven applicator.

5. The injection device according to claim 1, wherein said pneumatic damper is configured to substantially dampen kinetic energy imparted by the drive member to the syringe plunger from a cocked position of the plunger until the syringe has reached said second position.

6. The injection device according to claim 1, wherein said piston and cylinder are configured so that the inner surface of an end of the cylinder tapers radially outward with respect to an end of said piston, thereby establishing said second fluid flow path into said chamber following outward movement of the piston within the cylinder beyond a predefined point corresponding to said second position.

7. The injection device according to claim 6 and comprising an O-ring mounted on an external surface of said piston or on an internal surface of said cylinder and forming a substantially airtight seal between the piston and the cylinder up to said predefined point.

8. The injection device according to claim 1, wherein said piston extends coaxially inside said spring.

9. The injection device according to claim 1, wherein said piston head is fixed to the drive member.

10. The injection device according to claim 1, wherein said piston is formed integrally with said drive member.

11. The injection device according to claim 1, wherein said force applicator comprises a spring, and said drive member is generally cylindrical delimiting an interior within which said spring is located.

12. The injection device according to claim 11, said trigger mechanism being configured to engage with said drive member.

* * * * *